United States Patent [19]

Fenick

[11] Patent Number: 5,015,183
[45] Date of Patent: May 14, 1991

[54] LOCATING DEVICE AND METHOD OF PLACING A TOOTH IMPLANT

[76] Inventor: Thomas J. Fenick, Garwood Rd., Trumbull, Conn. 06611

[21] Appl. No.: 390,080

[22] Filed: Aug. 7, 1989

[51] Int. Cl.$^5$ .............................................. A61C 3/02
[52] U.S. Cl. .................................... 433/76; 433/173; 433/214
[58] Field of Search ................... 433/76, 75, 214, 213, 433/173, 215

[56] References Cited

U.S. PATENT DOCUMENTS

| | | | |
|---|---|---|---|
| 2,434,320 | 1/1948 | Karlstrom | 433/75 |
| 3,407,503 | 10/1968 | Nealon | 433/76 |
| 3,413,724 | 12/1968 | Segal | 433/214 |
| 3,600,810 | 8/1971 | Marshall et al. | 433/75 |

Primary Examiner—John J. Wilson
Attorney, Agent, or Firm—Arthur T. Fattibene; Paul A. Fattibene

[57] ABSTRACT

A method and device for placing an implant or artificial tooth in the most optimal bone structure by providing a radiology stent having a radial opaque grid disposed therein placed in the vicinity of the void where the implant is to be placed and taking a series of oblique X-rays at spaced intervals along the implant area utilizing the grid points produced on the X-ray for determining the optimum trajectory of the proposed implant, which is then related to a formed surgical stent having a guide for directing a drill bit in accordance with the trajectory established by the radiology stent.

12 Claims, 5 Drawing Sheets

LOCATING DEVICE AND METHOD OF PLACING A TOOTH IMPLANT

FIELD OF INVENTION

This invention is directed to a method of placing a tooth implant into a patient's mouth, and a device for precisely locating the implant into the most optimal bone structure of a patient's mouth.

1. Related Application

This application relates to an improvement to the method and device disclosed in my pending U.S. Pat. applicaton Ser. No. 07/309,188 filed Feb. 2, 1989 entitled Method of Placing A Tooth Implant and A Device for Locating the Optimum Position for Such Implant.

2. Problem and Prior Art

In dentistry, the use of placing tooth implants in a patient's mouth, in lieu of removable bridges and plates, has been gaining popularity. However, a problem in the art and science of placing tooth implants into a patient's mouth was finding or locating sufficient bone structure in which to fix the implant so as to obtain the most optimum results. As the bone structure and/or the density or mass thereof is not readily apparent, implants have frequently been placed into a location where there is insufficient bone structure to form a suitable anchoring position for the implant. The ultimate consequence thereof was a failure of the implant in a relatively brief period of time. Another difficulty noted with the prior known methods of placing an implant was that they generally required the special services of a general dentist practitioner, a lab technician and a dental surgeon, each performing their own limited functions, generally independently of one another and with no overall objective or uniform procedure to insure the optimum placement of the implant so as to obtain the maximum strength, occlusal and aesthetic results for the patient. As a result, tooth implants placed by prior techniques either failed because the implant was not seated in sufficient bone structure and/or the optimal occlusal and cosmetic aesthetic was not achieved due to the angulation of the implant fixture.

OBJECTS

An object of this invention is to provide a unified method for placing an implant into a patient's mouth so as to assure the coordination of all the procedures necessary for making a tooth implant having the most optimal strength, occlusal and aesthetic effects.

Another object is to provide a method for facilitating the drilling of a bore into the most optimal bone structure of a patient's jaw to define the most desirable seat for an implant fixture.

Another object is to provide a method for making the optimal occlusal and aesthetic determinations for a tooth implant along with determining the most optimum location for such implant into a patient's jaw.

Another object is to provide a casting of a patient's teeth formed with a guide for directing a drill along a predetermined trajectory into the most optimal bone structure of a patient's jaw to define the seat for a tooth implant fixture.

Another object is to provide a method and device for accurately transferring the most optimal implant trajectory as determined by an actual oblique X-ray of a patient's jaw to a model of the patient's teeth.

Another object is to provide a method and device for accurately transferring the optimal trajectory of an implant fixture from that determined by a model of the patient's teeth to the patient's mouth in preparation of drilling the implant seat in the patient's most optimal bone structure.

SUMMARY OF THE INVENTION

The foregoing objects and other features and advantages are attained by a method of imbedding a tooth implant into the most optimal bone structure of a patient's tooth by first making a model of a patient's teeth in the vicinity of the implant void. Upon completion of the model, one or more artificial teeth are positioned on the model in the implant void thereon to determine the occlusal and aesthetic positions of the contemplated implant. Upon the determination of the optimum arrangement of the contemplated implants, a casting or stent is made of the model with the artificial teeth in place. The casting or stent after setting is removed from the model and a radiopaque marker is positioned in the casting to extend horizontally along the center fossae of the implant void. Also disposed within the implant void of the casting or stent are a plurality of elongated X-ray opaque wires or strands which are spaced and secured horizontally in place to determine a grid of reference points in the region of the implant void of the casting or stent. The casting or stent so formed is then placed onto the teeth in the mouth of the patient an a diagnostic evaluation is made of a patient's mouth by taking a series of oblique X-ray views in the vicinity of the implant area to establish a trajectory into the most optimal bone structure for drilling the seat or bore into which the implant fixture is to be anchored. Such oblique X-rays will show the bone structure referenced horizontal to the grid points of the reference marks located in the stent or casting. A reference mark is then made on the oblique X-ray picture to correspond to the anterior/posterior and buccal/lingual tilts in accordance with the diagnostic evaluation. Upon completion of the X-ray evaluation, the casting or stent is removed from the patient mouth and cut cross-wise adjacent the point of implant as determined by the X-ray evaluation. The trajectory as established in the oblique X-ray is then transferred to the model by placing the cut stent onto the model and referencing the trajectory established in the oblique X-ray to the grid points in the stent. The stent, so cut, is position on the model and a hole is bored into the model along the trajectory determined by the diagnostic evaluation and transferred onto the model. A post is placed in the bore so drilled which extends beyond the hole. A sleeve guide is placed onto the extended end of the post whereby the axis of the sleeve is disposed in alignment with the determined trajectory of the hole. A second casting is made to the patient's model so as to fix the position of the guide sleeve relative to the patient's teeth. With the second casting in place onto one's teeth, the seat for the implant can be precisely drilled into the optimal bone structure as the guide sleeve functions to guide the drill bit along the predetermined trajectory to form the implant seat in the most optimal bone structure.

The device for perfecting the foregoing method comprises a first casting of the model of patient's teeth that has integrally disposed therein a plurality of radio X-ray opaque reference marks spaced horizontally to form a grid and which, when placed onto one's teeth for a diagnostic evaluation will reference the optimal bone structure relative thereto, and which points can then be transferred to the model of a patient's teeth to establish the optimal trajectory of the implant on the model, and a second stent or casting to transfer the trajectory of the implant seat formed on the model to the actual jaw of the patient.

FEATURES

A feature of this invention resides in the provision of a method in which the various procedures for making an implant can be standardized so as to coordinate the function of the dentist, lab technician and dental surgeon to assure the placement of a dental implant into the most optimal bone structure.

Another feature resides in the provision of a method for placing a tooth implant that is relatively simple and positive in application.

Another feature of this invention resides in the provision of a casting or stent having radiopaque points of reference which can be readily placed onto the teeth of a patient during a diagnostic evaluation so as to determine the optimal trajectory of an implant relative to the optimal bone structure of the patient.

Another feature of the invention resides in the construction of a stent or casting of a patient's teeth whereby the optimal trajectory as determined by the anterior/posterior angulation and buccal/lingual tilts in a diagnostic evaluation of a patient's mouth can be accurately transferred to a model of the patient's teeth.

Another feature resides in the provision of a method whereby the trajectory for placing an implant into the most optimal bone structure of a patient's jaw as determined by an X-ray evaluation can be accurately transferred onto the model of a patient's teeth into which the implant seat is formed in accordance with such established trajectory, and whereby the angulation of the implant bore or seat as so formed in the model can be accurately transferred to the jaw of the patient to receive the implant.

Another feature resides in the provision of a casting made of a patient's teeth in which guide sleeves are predeterminately disposed relative to the implant void so as to insure the drilling of the implant seat into the most optimal bone structure of the patient's jaw.

Another feature resides in the provision of a casting of a patient's teeth which can function as a permanent record for precisely relocating the implant seat.

Other features and advantages will become more readily apparent when considered in view of the drawing and following detailed description.

DETAILED SPECIFICATION

Referring to the drawings, there is illustrated the sequential steps for locating the most optimal position or location for the placement of an implant into a patient's mouth. An implant as used herein includes an implant fixture or post which is imbedded into the bone structure of a patient's jaw bone, and upon which an artificial tooth is constructed so as to simulate a patient's natural tooth. It will be understood that the method to be herein described can be utilized with any of the conventionally known implant fixtures. Implant as herein defined may also include the positioning of a post or fixture into a bone structure upon which a dental plate may be attached.

Figures 1, 2, 3:
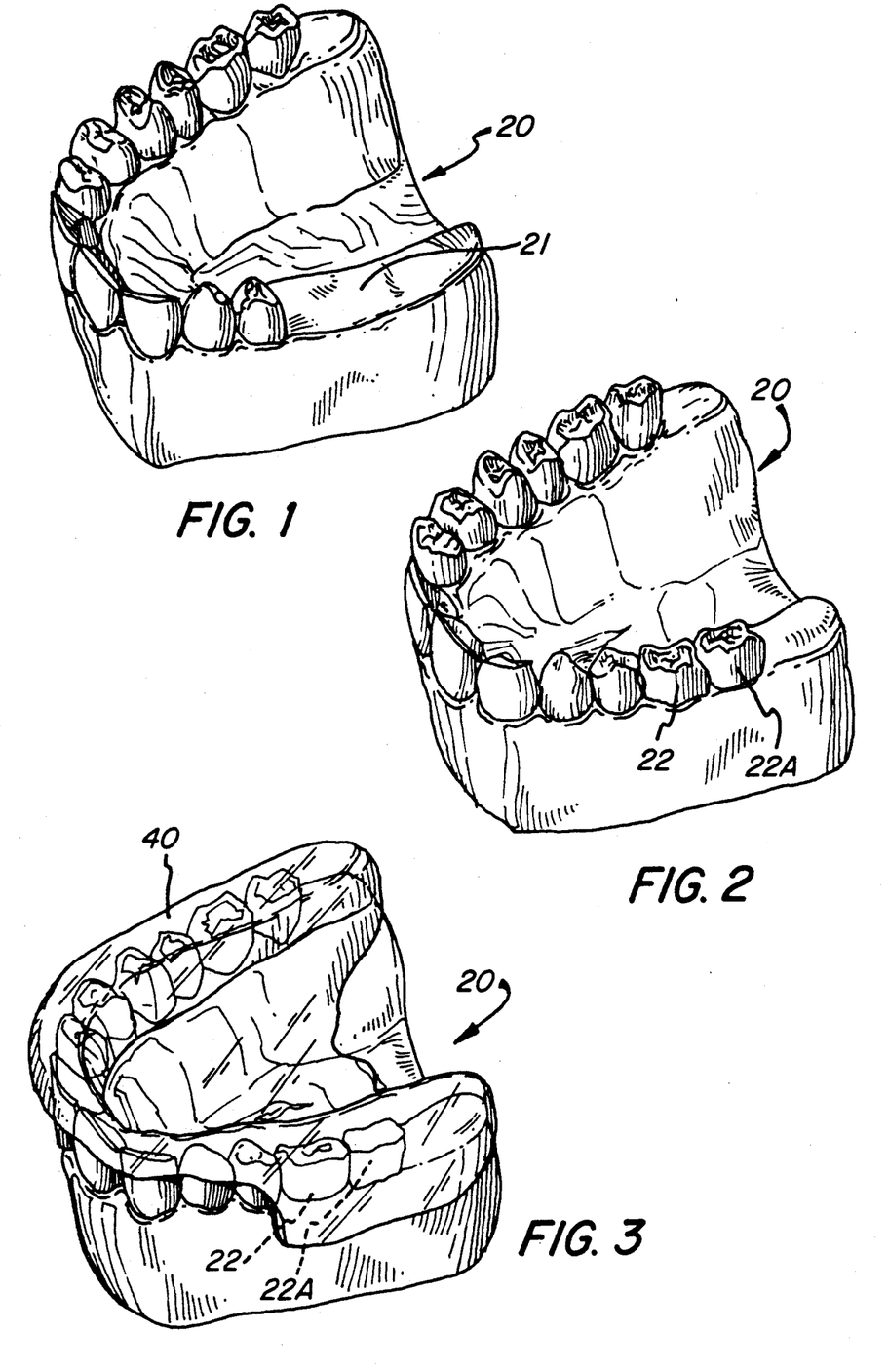
FIG. 1 is a perspective view of a model made from an impression of a patient's teeth illustrating the implant void.
FIG. 2 is a perspective view of the model of FIG. 1, showing artificial teeth located in the implant void.
FIG. 3 is a perspective view of FIG. 2 illustrating a casting or stent being formed of the model of a patient's teeth.

In accordance with the present invention, an impression is taken of a patient's teeth in the vicinity of the area in which the implant is to be made. From the impression taken, a model or cast of the patient's teeth is made. It will be understood that the model may be made in accordance with the known standard techniques of taking impressions and casting a model therefrom. FIG. 1 illustrates a casting 20 made of a patient's teeth and illustrating the implant void 21 where the contemplated implant is to be made. Depending upon the size of the void, one or more implants can be made in accordance with this invention. For illustrative purposes only, the implant void 21 is sized to accommodate two implants.

Figure 4:
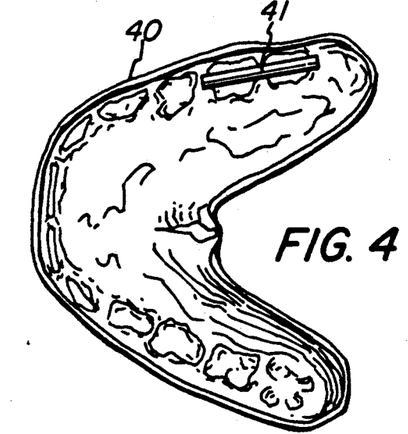
FIG. 4 illustrates a bottom view of the casting or stent having an radio opaque reference or wire located along the central fossae thereof.

After the model has been made as in FIG. 1, the dentist waxes in the implant void 21 the requisite number of artificial teeth, e.g., 22, 22A, that are compatible to the patient's original teeth, and a determination is thereby made to ascertain the optimal occlusal and aesthetic appearance of the proposed implants. Having thus determined the optimal occlusal and aesthetic effect for the contemplated implants a casting or stint 40 is made of the model 20 with the artificial teeth 22, 22A in place as shown in FIG. 2. After the casting or stint 40 has cured, it is removed from the model 20. FIG. 4 illustrates the bottom view of resulting casting or stint 40 showing the negative impression of the teeth taken from the model. In the vicinity of the implant area of the casting or stint 40, X-ray opaque impression formed, and is extended along the central fossae region of the teeth cavities formed in the negative impression of stint 40 as indicated in FIG. 4. In addition to the central fossae marking or strip 41, a plurality of additional radio opaque strips, e.g., 41A, 41B, 41C, 41D, 41E and 41F are placed in the implant void area of the stint 40. This is preferably accomplished as shown in FIG. 5.

Figure 5:
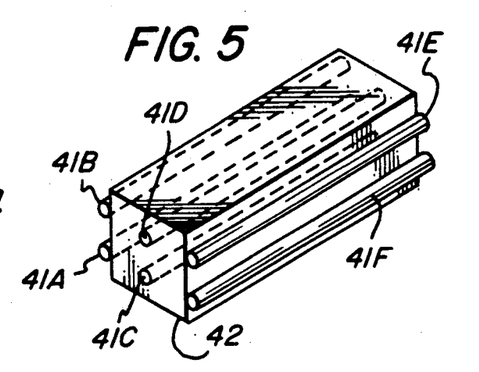
FIG. 5 is a perspective view of a detail of construction of the stint of FIG. 6.

Referring to FIG. 5, a block of material 42 transparent to X-rays provides a base to which a series or plurality of elongated strips of radio opaque materials or wires are extended therealong as indicated by 41A, 41B, 41C, 41D, 41E and 41F. This block of material, together with the radio opaque strips 41A-41F are then bonded to the stent 40 in the area 21 of the implant to complete the stent. Suitable markings or points of reference $R_1$ and $R_2$ are placed on the side of the stent to identify the area 21 of the implant void.

Figures 6, 7, 8:
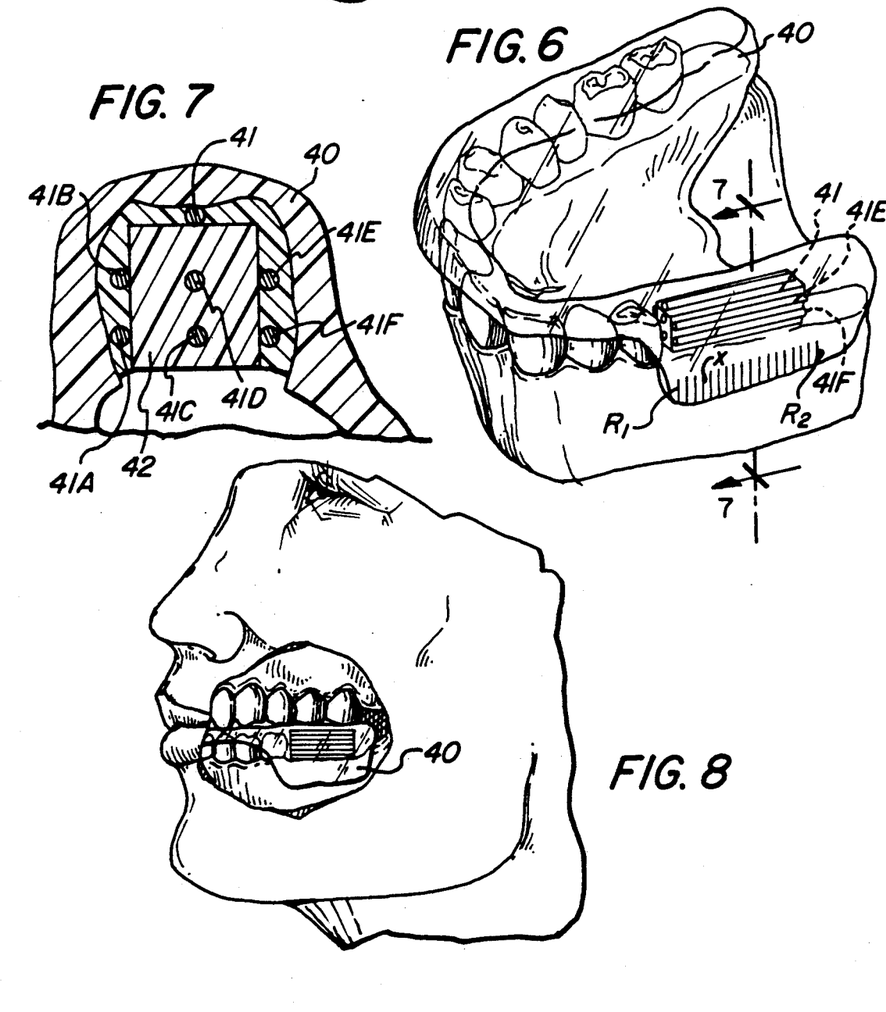
FIG. 6 is a perspective view of the complete casting or stent of FIG. 3.
FIG. 7 is a sectional view taken on line 7—7 on FIG. 6.
FIG. 8 is a perspective view of the casting or stint placed onto the teeth of a patient.
Figure 9:
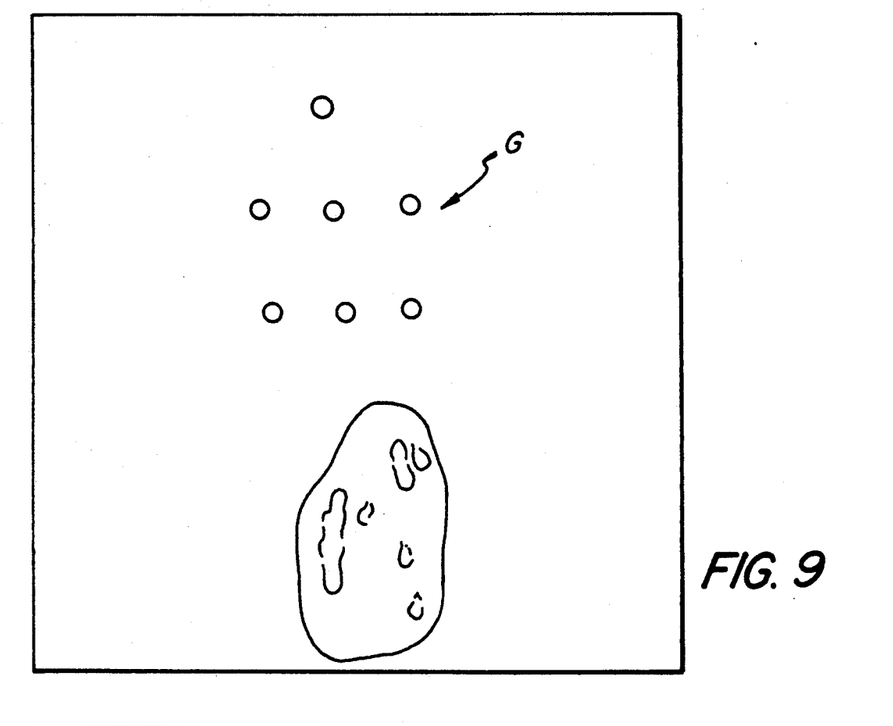
FIG. 9 is an oblique X-ray view taken of a patient's teeth with the casting or stint in place.
Figure 9A:
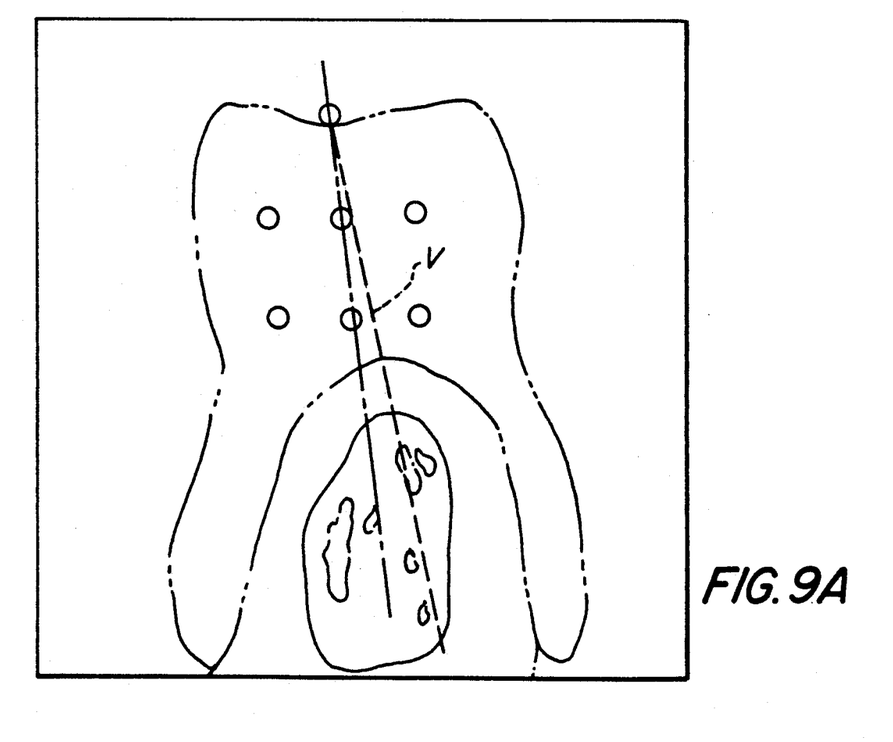
FIG. 9A is an oblique X-ray view showing the trajectory of a proposed implant relative to the most optimal bone structure.

The stent or casting 40 thus formed is then placed onto the teeth in the patient's mouth in preparation of the dentist or dental surgeon making the diagnostic evaluation of a patient's jaw structure to ascertain the location of the maximum bone density for locating the most optimal position for placing the implant fixture. With the stent or casting 40 in place on the patient's teeth, the dentist or dental surgeon takes a series of oblique X-ray pictures at intervals of approximately 1 mm. through the implant area as indicated at X on FIG. 6. This can readily be done with a Denta Scan, Cat-Scan or other suitable X-ray technique. Because of the X-ray opaque strips 41 to 41F located in the stint or casting 40, a series of X-rays such as shown in FIG. 9 result. As shown in FIG. 9, the X-ray oblique view will show the location of bone volume and density by reference to the grid/produced by the X-ray opaque strips located in the stent or casting 40. Utilizing the grid as defined by the X-ray opaque strips 41 to 41F, a dental surgeon can readily ascertain the direction and location of the implant seat to be drilled into the most optimal bone structure of the patient's mouth or jaw. FIG. 9A illustrates an oblique view taken in the void area of a patient's mouth to illustrate the determination of the vector/defining the most optimal location of the implant seat.

With the direction of the implant seat thus determined by the diagnostic evaluation, the dentist, lab technician or dental surgeon must now accurately transfer the direction and location of the implant seat as determined by the X-ray diagnostic evaluation to the model of the patient's teeth. This is attained by slicing or cutting the stint 40 transversely approximately 1.5 mm from the point 23A of the model, which is the starting point for the first implant seat as determined by optimal occlusal and aesthetic determination step as indicated in FIG. 2. The 1.5 mm dimension is approximately one-half the width of the drill bit utilized to form the implant seat. With the stent 40 thus cut transversely, the points of the grid as noted in the oblique X-ray of FIG. 9A are readily apparent on the stent. By utilizing the reference points 41 to 41F of the stent 40 as evident in FIG. 10, the direction or angulation of the implant seat as noted in FIG. 9A on the X-ray picture can be readily and accurately transferred to the model 20. With the angulation of the optimal bore seat location thus transferred to the model 20, the model is attached to a surveying table whereby both the table and the model 20 thereon is oriented relative to a drill press whereby a hole is drilled into the model along the line of trajectory established by the optimal anterior/posterior tilt and buccal/lingual tilt for the given implant site.

Figures 10, 11, 12:
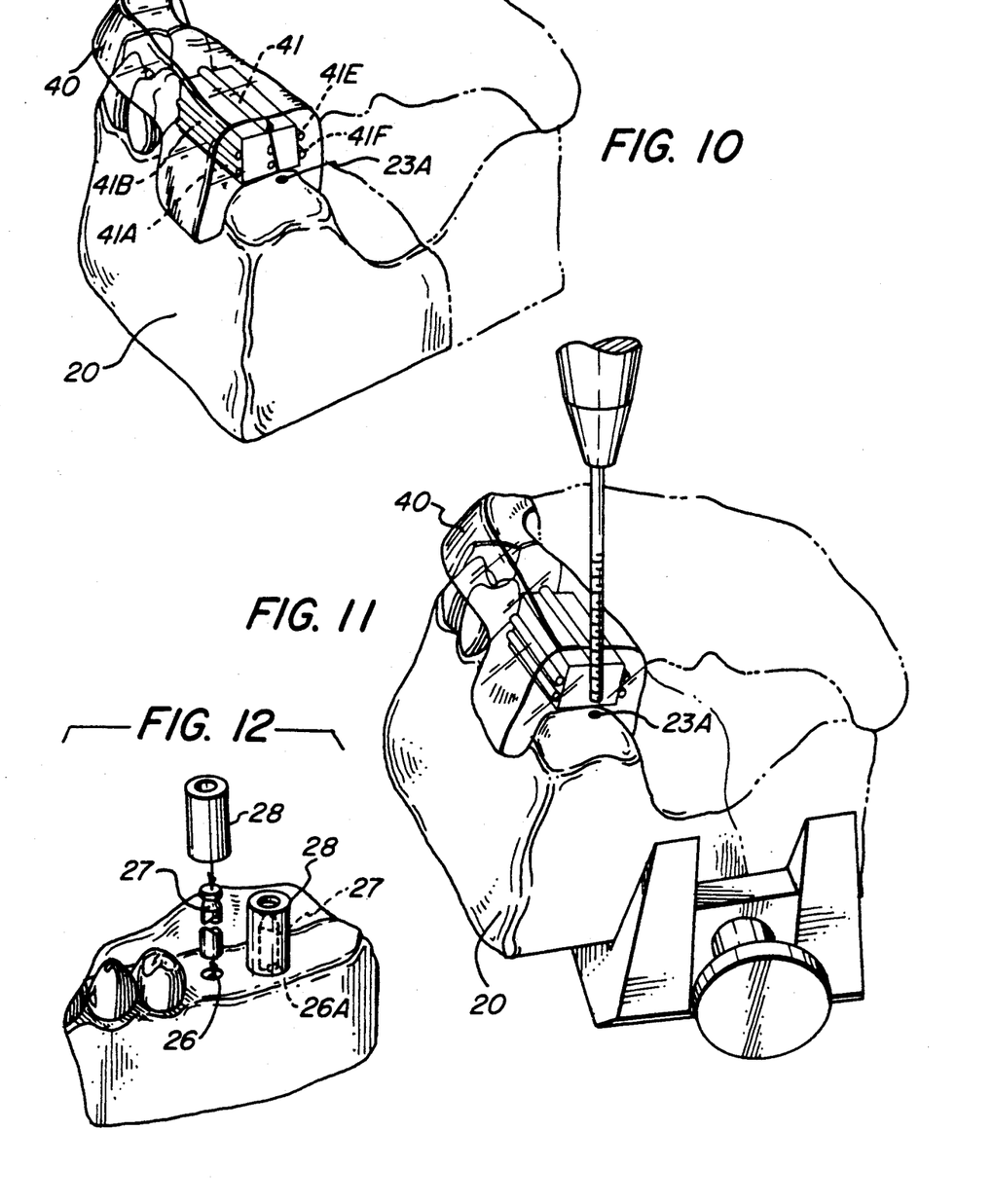
FIG. 10 is a perspective view of the stint or casting located on the model of a patient's teeth whereby the trajectory established by FIG. 9 is transferred onto the model.
FIG. 11 illustrates the orientation of the model as marked in FIG. 10 relative to a drill in preparation of boring a hole along the trajectory defined by the markings thereon.
FIG. 12 is a fragmentary showing of the model of FIG. 11 showing the drilled holes therein and the location of a guide sleeve relative thereto.

In the event a second or succeeding implant seat is required, the stent 40 is cut again transversely at a point approximately 1.5 mm from the second or succeeding implant seat area; and the procedure herein described is repeated to form a second hole as shown in FIG. 10.

Figures 13, 14, 14A, 15, 16, 17:
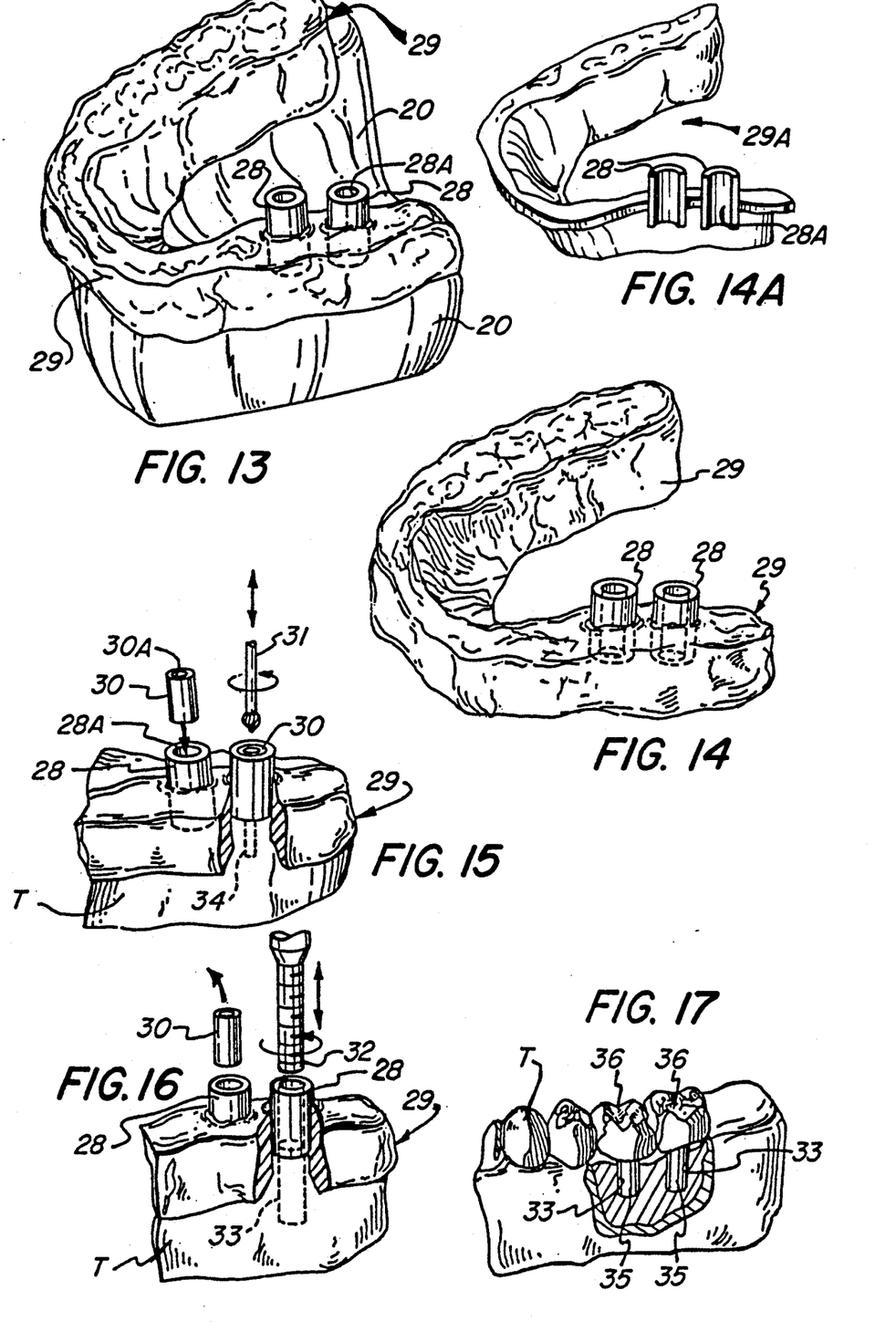
FIG. 13 is a view showing a casting made of the model which includes the guide sleeves as an integral part thereof.
FIG. 14 is a perspective view of the casting of FIG. 13.
FIG. 14A is a modified casting.
FIG. 15 is a fragmentary view of the casting of FIG. 12 placed onto the teeth in a patient's mouth to illustrate the drilling of a pilot bore for the implant.
FIG. 16 is a fragmentary view similar to FIG. 15 in preparation for drilling the main bore for the implant.
FIG. 17 is a view of the patient's teeth with the implant in place.

After the holes 26, 26A have been drilled into the model as herein described, a post 27 is inserted into each hole; so that the end of the post 27 extends beyond the end of the hole. A guide sleeve or tubular member 28 is placed over the extended end of each post 27. The size or internal bore of the respective guide sleeves 28 is dictated by the type of implant fixture used. The arrangement is such that the center of the respective guide sleeve is disposed in substantial alignment with the implant hole 26, 26A. The model with the guide sleeve in place is then prepared for making a second casting thereof. Accordingly, a casting material is placed onto the model to integrally include the respective guide sleeves in the resulting casting 29 as shown in FIG. 14. Thus, the casting 29 formed includes a negative impression of a patient's teeth including the implant void area in which the guide sleeves are positioned over the established trajectory by which the implant fixture is to be imbedded into the most optimum bone structure It will be understood that the guide sleeve 28 may be fixed or rendered vertically adjustable relative to the casting 29 to accommodate the removal or displacement of tissue whereby the guide sleeve 28 can be positioned as close as possible to the exposed bone structure. The guide sleeve could also be customized to meet individual surgeon's preferences, i.e., one-half tube diameter, sleeve or notched flatwall. It is preferred that the casting be made of a light curing resin material. However, the method may be performed utilizing known materials. To verify or check the angulation of the guide sleeves, a suitable radio opaque material is inserted into the bore of the guide sleeves whereby the angulation of the sleeve can be checked by a radiograph and compared with the results of the diagnostic evaluation previously made.

Once the cast 29 has been made, it is fitted to the patient's natural teeth which will locate the guide sleeves precisely over the implant area with the guide sleeve properly angled to guide a drill for drilling an implant bore or seat directly into a patient's bone structure along the established trajectory as determined by the patient's most optimal bone structure for receiving such implant.

With the casting 29 in place over the patient's natural teeth, T, a surgeon can drill an implant seat 33 into the patient's bone structure along the predetermined trajectory. If desired, the drilling of the implant seat can be made by first drilling a pilot bore 34 for the implant seat. Preferably, the drilling of the pilot bore 34 is made by locating a bushing or pilot sleeve 30 which is sized to be received within the bore 28A of the guide sleeve 28, the pilot sleeve or bushing 30 having a bore 30A sized to receive the pilot drill 31. After the pilot hole 34 has been formed, the pilot sleeve or bushing 30 is removed, and the pilot hole 34 redrilled by a drill size 32 sufficient to accommodate the implant fixture. While the forming of the implant seat 33 on the patient's bone structure has been described as a two step operation, it will be understood that the implant seat 33 can be formed by a single drilling operation or procedure. With the implant seat so formed, the axis thereof will conform to the trajectory established along the most optimal bone structure so as to assure maximum implant life.

After the implant seat 33 has been drilled as described, the implant fixture 35 is imbedded in the implant seat 33 in the manner prescribed therefor and the appropriate artificial tooth or tooth superstructure 36 is supported on the implant fixture 35 so imbedded to complete the implant procedure.

Upon completion of the implant, the casting 29 may be placed in the patient's record, and thus a permanent record is had of the patient's particular implant angulation.

Important to the foregoing described procedure is the casting of the stent 40 for ascertaining the optimal trajectory of the implant seat and the casting 29 which comprises an impression made of the patient's teeth. The casting or stents 40 and 29 thus comprises an integral molding or impression of just the top portion of the teeth and includes as an integral part thereof, the grid reference points in stent 40 and the respective guide sleeves in casting 29 which are angled to the trajectory determined by the patient's optimum bone structure.

In the event a patient's mouth is small and/or if there is insufficient head room for the surgeon to position the drill in the patient's mouth to align with the guide sleeve 28 in preparation for boring the fixture implant seat in the patient's jaw structure, the stent or casting 29 can be formed so as to permit the drill to be introduced sideways into the guide sleeve 28. This is attained by forming a partial casting 29A or by cutting the casting 29 longitudinally along a medial axis thereof. FIG. 14A illustrates a modified casting to provide a side entry to the guide sleeve or guide means 28. As shown in FIG. 14A, the casting can be initially formed to define only a partial casting as shown, or the casting 29 can be formed as herein described, and which is then cut longitudinally to define a guide sleeve having a side opening 28A for receiving the drill. In this manner, a surgeon can position the drill in situations when the headroom or space is otherwise restricted.

From the foregoing description, it will be apparent that the positioning of the implant fixture into the patient's optimum bone structure is rendered more accurate and positive, and that the described method and device in the form of the stent and casting 40 and 29 enables the dentist, lab technician and surgeon to coordinate their respective activities to insure the positioning of an implant that has the maximum strength and the proper occlusal and aesthetic appearance. The described procedure also eliminates the guesswork heretofore encountered in making an implant.

While the invention has been described with respect to a particular embodiment thereof, variations and modifications may be made without departing from the spirit or scope of the invention.

What is claimed is:

1. A method of imbedding a tooth implant comprising the steps of
    forming a stint comprising a negative impression of a patient's teeth in the vicinity of the implant area,
    locating a plurality of X-ray opaque strips in the negative impression of said stint in the vicinity of the implant area,
    placing the stint so formed on the teeth of the patient,
    taking a series of oblique X-rays for a diagnostic evaluation of a patient's jaw structure in the vicinity of the implant area with said stint in the patient's mouth,
    and plotting the optimal trajectory for an implant fixture by reference to the image points produced on said X-ray by said opaque strips.

2. The method as defined in claim 1 and including the step of transferring the trajectory plotted on said X-ray to a model of the patient's teeth.

3. The method as defined in claim 2 and including the step of drilling an implant seat in the model of the patient's teeth along trajectory transferred onto said model.

4. The method as defined in claim 3 and including the step of
    disposing a guide sleeve in co-axial alignment with the implant seat formed in said model,
    and forming a second negative impression to incorporate and fix therein the guide sleeve.

5. The method as defined in claim 4 and including the step of placing said second negative impression onto the patient's teeth, and
    utilizing said guide sleeve for guiding a drill bit in forming the implant seat in the patient's mouth.

6. A method for accurately forming an implant seat in the most optimal bone structure of a patient's mouth comprising the steps of
    forming a model of the patient's teeth adjacent the void area to receive an implant fixture,
    placing an artificial tooth on the model in the void area for determining the proper occlusal and aesthetic determinations,
    taking a negative impression of the model with the artificial teeth in place thereon,
    placing a radiopaqued marker along the central fossae of the negative impression in the void area,
    disposing a plurality of radio-opaqued markers spaced horizontally in the void area between the central fossae and the tissue side of said negative impression,
    placing the negative impression so formed onto a patient's teeth,
    making a diagnostic evaluation of the patient's bone structure with the negative impression in place on the patient's teeth by taking a series of oblique X-rays at transversely spaced intervals along the void area,
    determining the location of the most optimal bone structure for receiving the implant fixture on the X-ray,
    plotting the trajectory of a proposed implant by referencing the location of the most optimal bone structure to the image points formed of said radio opaqued markers of said negative impression,
    transferring the trajectory as determined by said oblique X-ray to the model of the patient's teeth by cutting said negative impression transversely adjacent to the site location of the implant seat, and noting the trajectory at the cut end of said negative impression by locating corresponding points of reference from said X-ray onto said cut end of said negative impression,
    placing the model and negative impression on a surveying table to orient the model relative to drill, and
    boring a hole in the model to coincide with the established trajectory, locating a guide sleeve in axial alignment with said hole, making a second negative impression of the model to include the guide sleeve therein, placing the second impression onto the teeth of the patient, and utilizing the guide sleeve as a guide for drilling the implant seat in the optimal bone structure of the patient as determined by the diagnostic evaluation.

7. A method of imbedding a tooth implant into the most optimal bone structure of a patient's mouth comprising the steps of forming a model of a patient's teeth to include the implant void, making a first negative impression of the model and implant void, locating in said first impression in the implant void thereof a plurality of spaced apart X-ray opaque strips to define points of reference cross-sectional thereof, placing said first impression onto the patient's teeth, void to obtain cross-sectional views of the patient's bone structure and said first impression whereby said radio opaque marker defines a reference grid on said X-rays, and utilizing said X-rays to determine the trajectory for seating an implant fixture in the patient's most optimal bone structure by referencing said bone structure to said grid.

8. The method as defined in claim 7 and including the step of transferring the trajectory as determined by said X-rays to said model by referencing the points of said X-ray to the points of said negative impression fitted to said model.

9. The method as defined in claim 8 and including the step of boring a hole in said model in alignment with said trajectory.

10. The method as defined in claim 9 and including making a second impression of said model having guide sleeves disposed in alignment with said holes bored in said model.

11. A dental stent comprising a negative impression of a patient's teeth including the void area for receiving a proposed implant fixture and a plurality of radiopaqued reference lines connected to said negative impression in said void area in spaced relationship relative to each other.

12. A dental stent as defined in claim 12 wherein said plurality of radipaqued lines includes one line extending along the central fossae of said negative impression, and the other of said radiopaqued lines being spacially disposed horizontally between said one line and the tissue side of said impression.

* * * * *